US007755042B1

(12) United States Patent
Toth et al.

(10) Patent No.: US 7,755,042 B1
(45) Date of Patent: Jul. 13, 2010

(54) AUGER ELECTRON SPECTROMETER WITH APPLIED MAGNETIC FIELD AT TARGET SURFACE

(75) Inventors: Gabor D. Toth, San Jose, CA (US); Rudy F. Garcia, Union City, CA (US); Chris Huang, Cupertino, CA (US); Niles Kenneth MacDonald, San Jose, CA (US); Mehran Nasser-Ghodsi, Hamilton, MA (US); Garrett Pickard, Mt. View, CA (US); Khashayar Shadman, Mt. View, CA (US); Wo-Tak Wu, Cupertino, CA (US); Ming Yu, Fremont, CA (US)

(73) Assignee: KLA-Tencor Corporation, San Jose, CA (US)

( * ) Notice: Subject to any disclaimer, the term of this patent is extended or adjusted under 35 U.S.C. 154(b) by 142 days.

(21) Appl. No.: 12/124,407

(22) Filed: May 21, 2008

Related U.S. Application Data

(60) Provisional application No. 61/046,317, filed on Apr. 18, 2008.

(51) Int. Cl.
*H01J 37/05* (2006.01)

(52) U.S. Cl. ............... 250/305; 250/306; 250/307; 250/310

(58) Field of Classification Search ............... 250/305, 250/306, 307, 310, 396 ML, 396 R
See application file for complete search history.

(56) References Cited

U.S. PATENT DOCUMENTS

| 4,882,486 | A | * | 11/1989 | Kruit | ............... 250/305 |
| 5,003,172 | A | | 3/1991 | Kruit et al. | |
| 6,747,279 | B2 | * | 6/2004 | Adamec | ............... 250/396 ML |
| 6,946,654 | B2 | | 9/2005 | Gerlach et al. | |
| 7,560,691 | B1 | * | 7/2009 | Gubbens | ............... 250/305 |

* cited by examiner

*Primary Examiner*—Kiet T Nguyen
(74) *Attorney, Agent, or Firm*—Okamoto & Benedicto LLP

(57) ABSTRACT

A scanning electron beam apparatus with an Auger spectrometer. The apparatus includes at least an electron column for generating a primary electron beam, a magnetic objective lens configured to focus the primary electron beam onto a surface of a target substrate, and a spectrometer configured to detect Auger electrons emitted from the surface of the target substrate. The magnetic objective lens applies a magnetic field strength greater than 10 Gauss and less than 50 Gauss at the surface of the target substrate. Other embodiments, aspects and features are also disclosed.

11 Claims, 3 Drawing Sheets

US 7,755,042 B1

AUGER ELECTRON SPECTROMETER WITH APPLIED MAGNETIC FIELD AT TARGET SURFACE

CROSS-REFERENCE TO RELATED APPLICATIONS

The present disclosure claims the benefit of U.S. provisional patent application No. 61/046,317, entitled "Auger Electron Spectrometer With Applied Magnetic Field At Target Surface," filed Apr. 18, 2008, by Gabor Toth, Rudy Garcia, Chris Huang, Nick MacDonald, Mehran Nasser Ghodsi, Garrett Pickard, Khashayar Shadman; Wo-Tak Wu, and Ming Yu, the disclosure of which is hereby incorporated by reference in its entirety.

BACKGROUND OF THE INVENTION

1. Field of the Invention

The present disclosure relates to Auger electron spectrometry and to electron beam apparatus.

2. Description of the Background Art

Auger spectrometry is a technique that uses a primary electron beam or other means, such as x-ray radiation, to probe a material surface. The primary electron beam or other means causes the emission of Auger electrons.

Auger electrons result from the following process in the material surface. When an electron is emitted from a core level of an atom, leaving a vacancy, an electron from a higher energy level may fall into the lower-energy-level vacancy. This results in a release of energy either in the form of an emitted photon or by ejecting another electron. Electrons ejected in this manner are called Auger electrons.

Auger electrons are detected by a spectrometer. The elements in the sample surface region may be determined from kinetic energies of the peaks in the Auger spectrum.

Auger electron spectrometers traditionally are incorporated into only non-magnetic type scanning electron microscopes (SEMs). In such SEMs, the magnetic focusing fields are either not present, fully contained or nearly fully contained inside the objective lens, and the sample is placed in a field-free or nearly field-free region below the lens. In such a system the Auger electrons travel in approximately straight lines from the sample, and the spectrometer's collection efficiency is determined largely by the solid angle of the spectrometer's entrance aperture and the spectrometer's angular position with respect to the sample surface.

Magnetic objective lenses are conventionally avoided for Auger spectrometry because such lenses typically immerse the sample in a substantial magnetic field. Due to the presence of such magnetic fields, the Auger electrons cannot travel in substantially straight and un-deflected lines from the sample surface to an Auger spectrometer, located outside the SEM column.

SUMMARY

Figure 1:
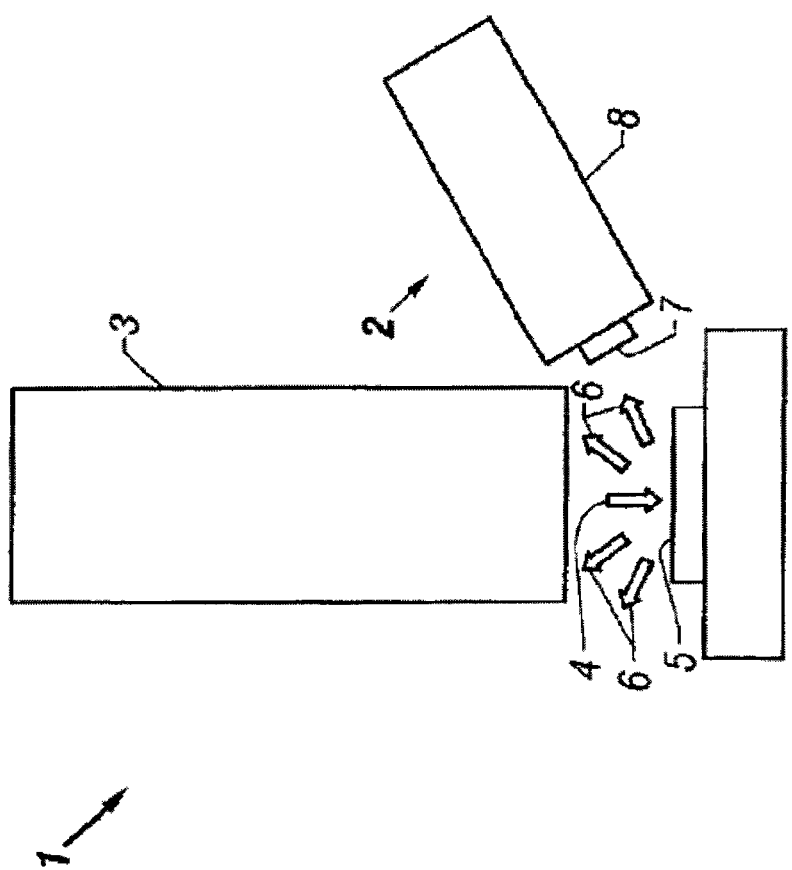
FIG. 1 is a schematic diagram of a scanning electron microscope apparatus with an Auger electron spectrometer in accordance with an embodiment of the invention.

A scanning electron beam apparatus with an Auger spectrometer. The apparatus includes at least an electron column for generating a primary electron beam, a magnetic objective lens configured to focus the primary electron beam onto a surface of a target substrate, and a spectrometer configured to detect Auger electrons emitted from the surface of the target substrate. The magnetic objective lens applies a magnetic field strength greater than 10 Gauss and less than 50 Gauss at the surface of the target substrate.

A method of performing high-resolution Auger electron spectrometry. The method includes at least forming a primary electron beam in an electron beam column, using an magnetic objective lens to focus the primary electron beam onto a surface of a target substrate, and detecting Auger electrons emitted from the surface of the target substrate using a spectrometer. The magnetic objective lens applies a magnetic field strength greater than 10 Gauss and less than 50 Gauss at the surface of the target substrate.

Other embodiments, aspects and features are also disclosed.

DETAILED DESCRIPTION

As discussed above in the Description of the Background Art, Auger spectrometry is conventionally performed without using field at the target surface. For example, a typical SEM apparatus with Auger spectroscopic capability may be configured with purely electrostatic optics.

The conventional approach is generally to reduce any magnetic field to a few Gauss or less in strength both at the probed surface area and in the vicinity of the spectrometer entrance. This is because it is expected that magnetic fields above a few Gauss in strength would result in significant Auger electron loss and/or distortion of the Auger spectrum.

However, as disclosed herein, an unexpected result has been found that the effect of moderate magnetic flux density at the wafer surface can be compensated by proper alignment of the spectrometer other than the true geometric optimum.

It is certainly true that large magnetic field strengths at the probed area will prevent electron detection outside the probe forming optics. It is also true that even small magnetic field strengths can alter the trajectory of low-energy Auger electrons and distort the spectra.

Nevertheless, magnetic field strengths in the range of 10 Gauss to 50 Gauss in the region above the sample surface may be compensated reliably by detector alignment and proper aperture selection with insubstantial electron loss. Furthermore, the resulting spectra surprisingly shows less (not more) distortion than spectra obtained in the absence of a substantial magnetic field. These unexpected results are shown to be repeatable in experiments by the applicants.

Advantageously, this phenomenon enables one to improve the spatial resolution of the Auger spectrometry while preserving the elemental sensitivity of the Auger detector. This is because the spot size of the electron probe may be significantly reduced by using a magnetic objective lens which leaks considerable magnetic field strength to the probed area or even to the detector area itself.

Figure 2:
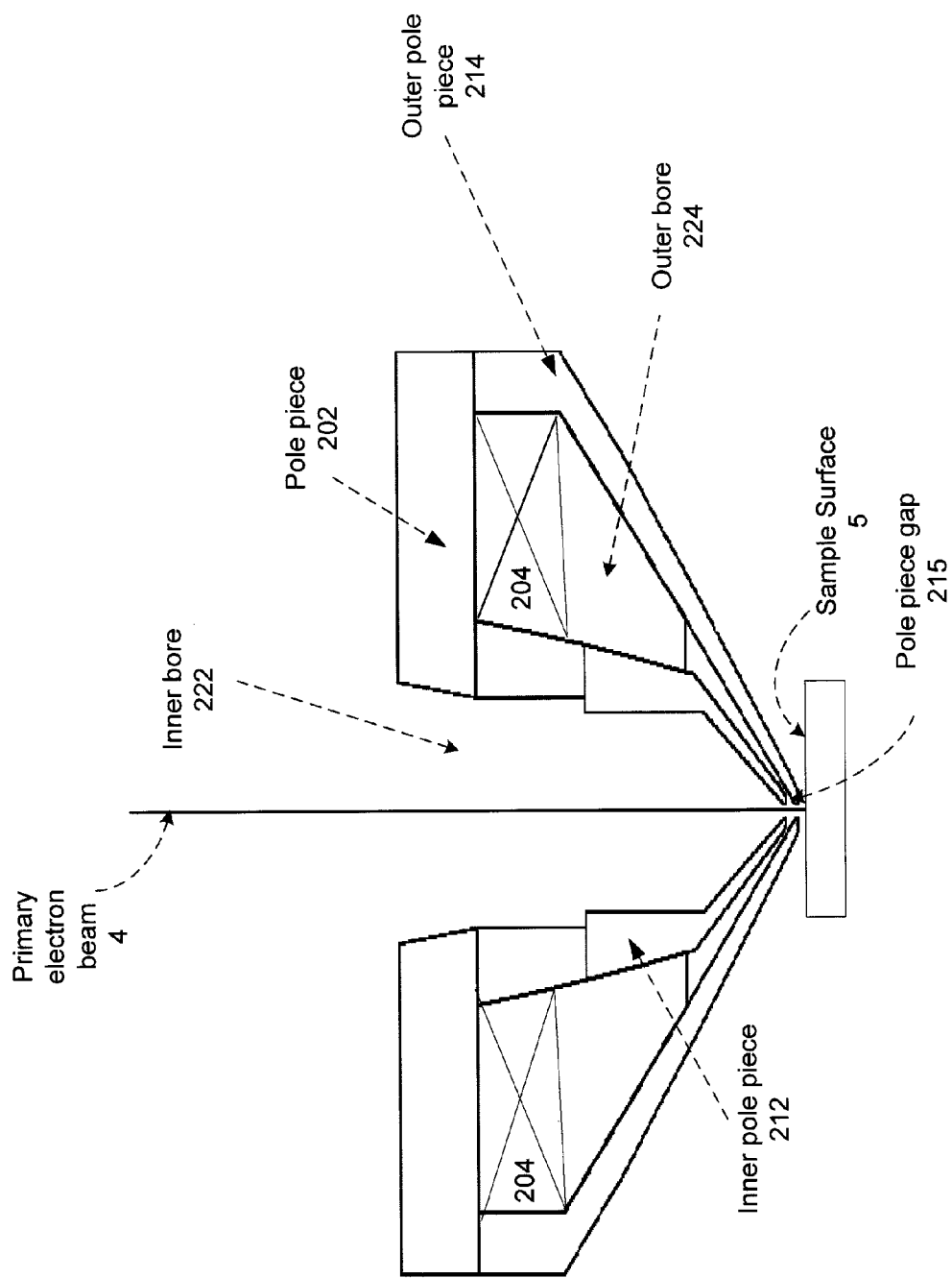
FIG. 2 is a more detailed cross-sectional diagram depicting a magnetic objective lens of the scanning electron microscope apparatus in accordance with an embodiment of the invention.

FIG. 1 is a schematic diagram of a scanning electron microscope apparatus 1 with an Auger spectrometer system 2 in accordance with an embodiment of the invention. An electron column 3 is configured with an electron source and electron lenses to generate a primary electron beam 4 and to focus the primary electron beam 4 onto a sample surface 5. Secondary electrons 6 are collected through an opening 7 (the spectrometer entrance) of the Auger electron system 2 and transferred to an analyzer 8. As shown, the Auger electron system 2 may be configured to the side of the primary electron beam 4. While one Auger detector configuration is shown in FIG. 1, other Auger detector configurations may also be implemented FIG. 2 is a more detailed cross-sectional diagram depicting a magnetic objective lens of the scanning electron microscope apparatus 1 similar to the embodiment of the invention. As shown, the primary electron beam 4 travels down an optical axis and through the magnetic objective lens to become focused upon the surface 5 of a target substrate. A magnetic pole piece 202 of the objective lens is configured about the optical axis, with a pole piece gap 215 in the form of a ring around the optical axis. The pole piece 202 may be formed using an inner bore 222 and an outer bore 224 so as to define an inner pole piece 212 and an outer pole piece 214. The pole piece gap 215 may extend from a tip of the inner pole piece 212 to a tip of the outer pole piece 214. An electromagnetic device (coil) 204 may be configured within the outer bore 224 so as to generate a magnetic field which extends from the pole piece gap 215 immerses the surface 5 of the target substrate. In the particular embodiment shown in FIG. 2, the inner and outer bores have the same (or approximately the same) width.

In accordance with one embodiment, control of the applied magnetic field at the sample may be achieved by changing the position of the outer pole piece 214 with respect to the inner pole piece 212 as well as the size of the outer pole piece bore 224.

In a pure axial lens system, the surface of the frustum defined by the inner and outer pole piece bores is parallel to the optical axis and degrades to a cylinder. On the other hand, in a perfectly radial lens system, this frustum degrades to a ring with a radius perpendicular to the optical axis. In accordance with an embodiment of the invention, the amount of leakage magnetic field from the magnetic objective lens towards the target surface may be controlled by variation of the pole piece geometry in between these two extremes (pure axial and pure radial). The absolute value of the leakage field is also determined by the excitation level (working distance and beam energy) as well as the outer pole piece.

Figure 3:
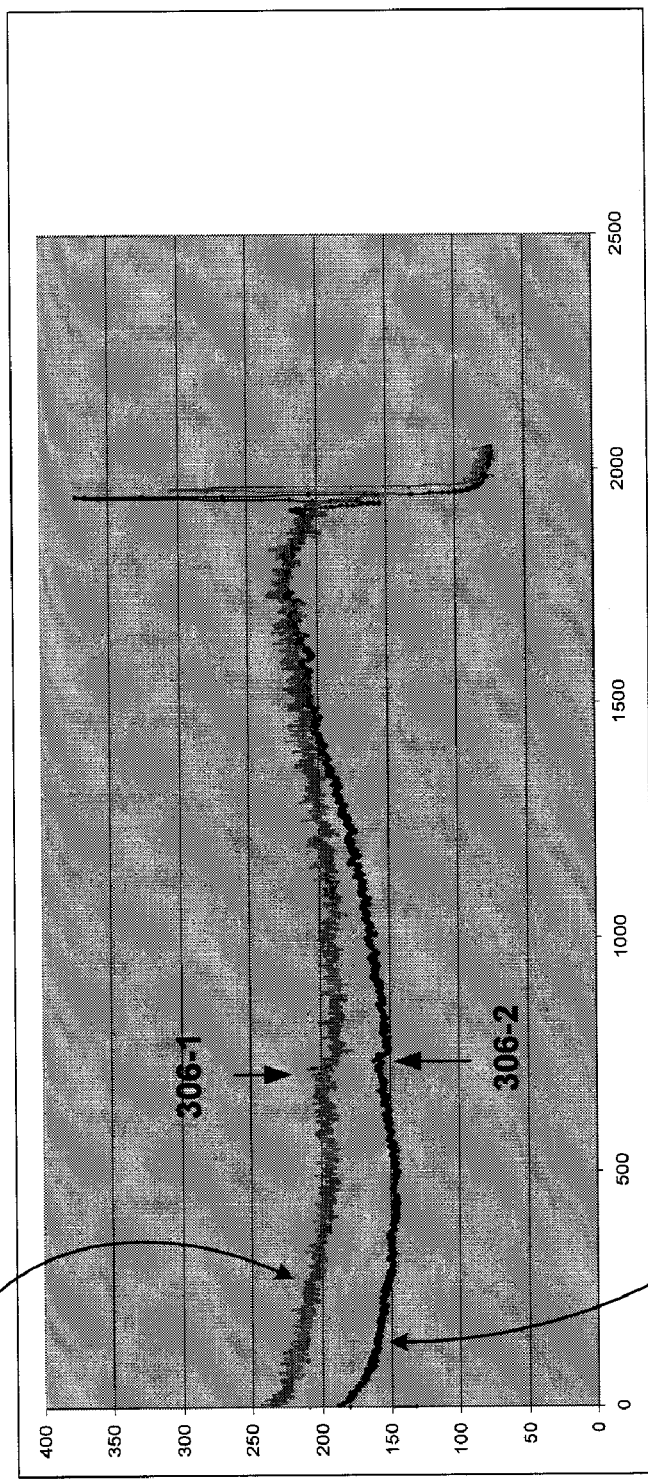
FIG. 3 compares electron spectra with no applied magnetic field as per conventional Auger spectrometry and with an applied magnetic field in accordance with an embodiment of the invention.

FIG. 3 compares electron spectra with no applied magnetic field 302 as per conventional Auger spectrometry and with an applied magnetic field 304 in accordance with an embodiment of the invention. Note, even in the case of no applied magnetic field, a very small magnetic field (for example, a few Gauss from the Earth's magnetic field) is typically present.

Unexpectedly, spectra acquired with "applied magnetic field", after proper detector alignment shows similar qualities as the one acquired with "no applied magnetic field" spectrum 302. For example, the Auger peaks corresponding to oxygen are more clearly seen and better defined in the applied magnetic field spectrum 304 (see peak labeled 306-2) than in the no applied magnetic field spectrum 302 (see peak labeled 306-1). Other similar spectra were obtained by the applicants showing similar results.

An embodiment of the apparatus 1 which was used to obtain the electron spectra of FIG. 3 is configured to acquire the Auger spectrum in a non-UHV (i.e. non ultra high vacuum) environment. The embodiment also used a parallel Auger spectrometer 8 which required accurate alignment with the probe. The spectrometer position was optimized for collection with an applied magnetic field in an approximate range of 10 to 50 Gauss in strength.

CONCLUSION

As disclosed herein, applicants have concluded that an Auger electron spectrometer with applied magnetic fields in a range of ten to fifty Gauss in strength at the target surface can provide good quality Auger spectrum. Applicants have achieved these results by applying the magnetic field in a range of ten to fifty Gauss and then aligning the spectrometer detector system to optimize the collection of Auger electrons.

Applicants believe that applied magnetic fields of greater than about fifty Gauss would likely be difficult to compensate for with alignment, and that applied magnetic fields of less than about ten Gauss would have only minor effect in terms of spot size reduction (and hence little improvement in spatial resolution).

The above-described diagrams are not necessarily to scale and are intended be illustrative and not limiting to a particular implementation. Specific dimensions, geometries, and lens currents of the magnetic objective lens will vary and depend on each implementation.

The above-described technique may be used, for example, in an automatic inspection and defect analysis system and applied to the inspection and review of wafers, X-ray masks and similar substrates in a production environment. Other uses are also possible.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A scanning electron beam apparatus with an Auger spectrometer, the apparatus comprising:
    an electron column for generating a primary electron beam;
    a magnetic objective lens configured to focus the primary electron beam onto a surface of a target substrate; and
    a spectrometer configured to detect Auger electrons emitted from the surface of the target substrate,
    wherein the magnetic objective lens applies a magnetic field strength greater than 10 Gauss and less than 50 Gauss at the surface of the target substrate.

2. The apparatus of claim 1, wherein the magnetic objective lens comprises an inner pole piece bore and an outer pole piece bore, the outer pole piece bore forming a pole piece gap facing towards or partially towards the surface of the target substrate.

3. The apparatus of claim 2, wherein the magnetic objective lens further comprises an electromagnetic device within the outer pole piece bore.

4. The apparatus of claim 2, wherein the magnetic objective lens further comprises an inner pole piece and an outer pole piece, wherein the pole piece gap comprises a gap extending from a tip of the inner pole piece to a tip of the outer pole piece.

5. The apparatus of claim 1, wherein the position of the spectrometer is changed depending upon the magnetic field strength applied.

6. The apparatus of claim 1, wherein the spectrometer comprises a parallel Auger spectrometer.

7. A method of performing high-resolution Auger electron spectrometry, the method comprising:
   forming a primary electron beam in an electron beam column;
   using a magnetic objective lens to focus the primary electron beam onto a surface of a target substrate; and
   detecting Auger electrons emitted from the surface of the target substrate using a parallel Auger spectrometer, wherein the magnetic objective lens applies a magnetic field strength greater than 10 Gauss and less than 50 Gauss at the surface of the target substrate.

8. The method of claim 7, wherein the magnetic objective lens comprises an inner pole piece bore and an outer pole piece bore, the outer pole piece bore forming a pole piece gap facing towards the surface of the target substrate.

9. The method of claim 8, wherein the magnetic objective lens further comprises an electromagnetic device within the outer pole piece bore.

10. The method of claim 8, wherein the magnetic objective lens further comprises an inner pole piece and an outer pole piece, wherein the pole piece gap comprises a gap extending from a tip of the inner pole piece to a tip of the outer pole piece.

11. The method of claim 7, further comprising:
   aligning a position of the parallel Auger spectrometer depending upon the magnetic field strength applied.

* * * * *